United States Patent [19]
Kinet et al.

[11] Patent Number: 5,639,660
[45] Date of Patent: Jun. 17, 1997

[54] POLYPEPTIDE AND DNA SEQUENCE CORRESPONDING TO THE HUMAN RECEPTOR WITH HIGH AFFINITY FOR IGE

[75] Inventors: Jean Pierre Kinet, Bethesda, Md.; Jarema Peter Kochan, Verona, N.J.

[73] Assignees: Hoffmann-La Roche Inc., Nutley, N.J.; The United States of America as represented by the Department of Health and Human Services, Washington, D.C.

[21] Appl. No.: 160,457

[22] Filed: Feb. 24, 1988

[51] Int. Cl.⁶ .............................. C12N 1/21; C12N 5/10; C12N 15/12
[52] U.S. Cl. .................... 435/252.3; 435/69.1; 435/69.7; 435/320.1; 536/23.5
[58] Field of Search .............................. 536/27; 435/69.1, 435/172.3, 252.3, 243, 68.1; 530/387, 350

[56] References Cited

PUBLICATIONS

P.N.A.S. 78(11): 6613–6617, Nov. 1981, Suggs et. al. Use of Synthetic Oligonucleotides as Hybridization Probes: Isolation of Cloned cDNA Sequences for Human $B_2$–Microglobin.

J. Biol. Chem. 256(15):7990–7997, Aug. 10, 1981, Hewick et. al. A Gas–Liquid Solid Phase Peptide and Protein Sequenator.
Science 222:778–782, Nov. 18, 1983, Young and Davis, Yeast RNA Polymerase II Genes: Isolation with Antibody Probes.
Mol. Immunol. 21(12) 1167–1173, 1984, Metzger et. al. Analysis of the Structure and Function of the Receptor for Immunoglobulin E.
J. Biol. Chem. 261(25) 11823–11831, Sep. 5, 1986, Basciano et al. Monoclonal Antibodies that Inhibit IgE Binding.
Kochan, J. et al 1988 (Apr. 25) Nucleic Acids Research 16: 3584.
Shimizu A et al 1988 (Mar.) PNAS 85: 1907–1911.
Liu F–T et al 1988 (Aug.) PNAS 85: 5639–43.
Kinet, et al., *Biochemistry*, 26:4605 (1987).
Alcaraz, et al., *Biochemistry*, 26:2569 (1987).
Reuetch, et al., *Science*, 234:718 (1986).

*Primary Examiner*—John Ulm
*Attorney, Agent, or Firm*—George W. Johnston; Dennis P. Tramaloni; Bruce A. Pokras

[57] ABSTRACT

A Polypeptide and DNA Sequence corresponding to the human receptor high affinity receptor for IgE as well as replicable microbial expression vehicles, transformed microorganisms, and cultures of microbial cells which produce this polypeptide.

7 Claims, 6 Drawing Sheets

```
TACTAAGAGTCTCCAGCATCCTCCACCTGTCTACCACCGAGCATGGG

GAAGAAG ATG GCT CCT GCC ATG GAA TCC CCT ACT CTA
        MET Ala Pro Ala Met Glu Ser Pro Thr Leu
                                              10

TTA GCA¹ GTC CCT CAG AAA CCT AAG GTC TCC TTG AAC
Leu Ala Val Pro Gln Lys Pro Lys Val Ser Leu Asn
               30

CTT ACA TGT AAT GGG AAC AAT TTC TTT GAA GTC AGT
Leu Thr Cys Asn Gly Asn Asn Phe Phe Glu Val Ser
        50                                  60

ACA AAT TCA AGT TTG AAT ATT GTG AAT GCC AAA TTT
Thr Asn Ser Ser Leu Asn Ile Val Asn Ala Lys Phe
                        80

AAT GAG AGT GAA CCT GTG TAC CTG GAA GTC TTC AGT
Asn Glu Ser Glu Pro Val Tyr Leu Glu Val Phe Ser
    100                                     110

GAG GGC CAG CCC CTC TTC CTC AGG TGC CAT GGT TGG
Glu Gly Gln Pro Leu Phe Leu Arg Cys His Gly Trp
                130

GGT GAA GCT CTC AAG TAC TGG TAT GAG AAC CAC AAC
Gly Glu Ala Leu Lys Tyr Trp Tyr Glu Asn His Asn
    150                                     160

TAC TAC TGT ACG GGC AAA GTG TGG CAG CTG GAC TAT
Tyr Tyr Cys Thr Gly Lys Val Trp Gln Leu Asp Tyr
                    180

CGT GAG AAG TAC TGG CTA CAA TTT TTT ATC CCA TTG
Arg Glu Lys Tyr Trp Leu Gln Phe Phe Ile Pro Leu
    200                                     210

ATC TCA ACT CAG CAG CAG GTC ACA TTT CTC TTG AAG
Ile Ser Thr Gln Gln Gln Val Thr Phe Leu Leu Lys
                        230

CAT CCT AAG CCA AAC CCC AAA AAC AAC TGATATAATTA
His Pro Lys Pro Asn Pro Lys Asn Asn
        250

CAATTGTCAAACACAGCTTGCAATATACATAGAAACGTCTGTGCTCA

TAATAGTAAGTGCTCAATTAACATTGGTTGAATAAATGAGAGAATGA

AATATAAAACCATGTAACAGAATGCTTCTGAGTAAAAAAAAAAAAAA
```

```
CTATATTTGAAGCCTTAGATCTCTCCAGCACAGTAAGCACCAGGAGTCCAT    99

CTG TGT GTA GCC TTA CTG TTC TTC GCT CCA GAT GGC GTG    175
Leu Cys Val Ala Leu Let Phe Phe Ala Pro Asp Gly Val
                                20

CCT CCA TGG AAT AGA ATA TTT AAA GGA GAG AAT GTG ACT    250
Pro Pro Trp Asn Arg Ile Phe Lys Gly Glu Asn Val Thr
                        40

TCC ACC AAA TGG TTC CAC AAT GGC AGC CTT TCA GAA GAG    325
Ser Thr Lys Trp Phe His Asn Gly Ser Leu Ser Glu Glu
                                        70

GAA GAC AGT GGA GAA TAC AAA TGT CAG CAC CAA CAA GTT    400
Glu Asp Ser Gly Glu Tyr Lys Cys Gln His Gln Gln Val
                            90

GAC TGG CTG CTC CTT CAG GCC TCT GCT GAG GTG GTG ATG    475
Asp Trp Leu Leu Leu Gln Ala Ser Ala Glu Val Val Met
                                    120

AGG AAC TGG GAT GTG TAC AAG GTG ATC TAT TAT AAG GAT    550
Arg Asn Trp Asp Val Tyr Lys Val Ile Tyr Tyr Lys Asp
                140

ATC TCC ATT ACA AAT GCC ACA GTT GAA GAC AGT GGA ACC    625
Ile Ser Ile Thr Asn Ala Thr Val Glu Asp Ser Gly Thr
                                    170

GAG TCT GAG CCC CTC AAC ATT ACT GTA ATA AAA GCT CCG    700
Glu Ser Glu Pro Leu Asn Ile Thr Val Ile Lys Ala Pro
                190

TTG GTG GTG ATT CTG TTT GCT GTG GAC ACA GGA TTA TTT    775
Leu Val Val Ile Leu Phe Ala Val Asp Thr Gly Leu Phe
                                220

ATT AAG AGA ACC AGG AAA GGC TTC AGA CTT CTG AAC CCA    850
Ile Lys Arg Thr Arg Lys Gly Phe Arg Leu Leu Asn Pro
                    240

CTCAAGAAATATTTGCAACATTAGTTTTTTTCCAGCATCAGCAATTGCTACT    940

AGGATTTATAGAAATGCTTCATTAAACTGAGTGAAACTGGTTAAGTGGCATG    1039

ATAGATTCATTTATTAGCATTTGTAAAAGAGATGTTCAATTTCAATAAAATA    1138

AAAAAAAAAAAA                                            1198
```

TACTAAGAGTCTCCAGCATCCTCCACCTGTCTACCACCGAGCATGGG

GAAGAAG ATG GCT CCT GCC ATG GAA TCC CCT ACT CTA
        MET Ala Pro Ala Met Glu Ser Pro Thr Leu
                                                            10

TTA GCA¹ GTC CCT CAG AAA CCT AAG GTC TCC TTG AAC
Leu Ala Val Pro Gln Lys Pro Lys Val Ser Leu Asn
                  30

CTT ACA TGT AAT GGG AAC AAT TTC TTT GAA GTC AGT
Leu Thr Cys Asn Gly Asn Asn Phe Phe Glu Val Ser
       50                                      60

ACA AAT TCA AGT TTG AAT ATT GTG AAT GCC AAA TTT
Thr Asn Ser Ser Leu Asn Ile Val Asn Ala Lys Phe
                            80

AAT GAG AGT GAA CCT GTG TAC CTG GAA GTC TTC AGT
Asn Glu Ser Glu Pro Val Tyr Leu Glu Val Phe Ser
       100                                 110

GAG GGC CAG CCC CTC TTC CTC AGG TGC CAT GGT TGG
Glu Gly Gln Pro Leu Phe Leu Arg Cys His Gly Trp
                  130

GGT GAA GCT CTC AAG TAC TGG TAT GAG AAC CAC AAC
Gly Glu Ala Leu Lys Tyr Trp Tyr Glu Asn His Asn
       150                                 160

TAC TAC TGT ACG GGC AAA GTG TGG CAG CTG GAC TAT
Tyr Tyr Cys Thr Gly Lys Val Trp Gln Leu Asp Tyr
                          180

CGT GAG AAG TAC TGG CTA CAA TTT TTT ATC CCA TTG
Arg Glu Lys Tyr Trp Leu <u>Gln Phe Phe Ile Pro Leu</u>
       200                               210

ATC TCA ACT CAG CAG CAG GTC ACA TTT CTC TTG AAG
<u>Ile</u> Ser Thr Gln Gln Gln Val Thr Phe Leu Leu Lys
                            230

CAT CCT AAG CCA AAC CCC AAA AAC AAC TGATATAATTA
His Pro Lys Pro Asn Pro Lys Asn Asn
      250

CAATTGTCAAACACAGCTTGCAATATACATAGAAACGTCTGTGCTCA

TAATAGTAAGTGCTCAATTAACATTGGTTGAATAAATGAGAGAATGA

AATATAAAACCATGTAACAGAATGCTTCTGAGTAAAAAAAAAAAAAA

FIG. 1A

```
      CTATATTTGAAGCCTTAGATCTCTCCAGCACAGTAAGCACCAGGAGTCCAT              99

CTG TGT GTA GCC TTA CTG TTC TTC GCT CCA GAT GGC GTG             175
      Leu Cys Val Ala Leu Let Phe Phe Ala Pro Asp Gly Val
                                          20

CCT CCA TGG AAT AGA ATA TTT AAA GGA GAG AAT GTG ACT             250
      Pro Pro Trp Asn Arg Ile Phe Lys Gly Glu Asn Val Thr
                          40

TCC ACC AAA TGG TTC CAC AAT GGC AGC CTT TCA GAA GAG             325
      Ser Thr Lys Trp Phe His Asn Gly Ser Leu Ser Glu Glu
                                              70

GAA GAC AGT GGA GAA TAC AAA TGT CAG CAC CAA CAA GTT             400
      Glu Asp Ser Gly Glu Tyr Lys Cys Gln His Gln Gln Val
                              90

GAC TGG CTG CTC CTT CAG GCC TCT GCT GAG GTG GTG ATG             475
      Asp Trp Leu Leu Leu Gln Ala Ser Ala Glu Val Val Met
                                                 120

AGG AAC TGG GAT GTG TAC AAG GTG ATC TAT TAT AAG GAT             550
      Arg Asn Trp Asp Val Tyr Lys Val Ile Tyr Tyr Lys Asp
                           140

ATC TCC ATT ACA AAT GCC ACA GTT GAA GAC AGT GGA ACC             625
      Ile Ser Ile Thr Asn Ala Thr Val Glu Asp Ser Gly Thr
                                                 170

GAG TCT GAG CCC CTC AAC ATT ACT GTA ATA AAA GCT CCG             700
      Glu Ser Glu Pro Leu Asn Ile Thr Val Ile Lys Ala Pro
                           190

TTG GTG GTG ATT CTG TTT GCT GTG GAC ACA GGA TTA TTT             775
      Leu Val Val Ile Leu Phe Ala Val Asp Thr Gly Leu Phe
                                              220

ATT AAG AGA ACC AGG AAA GGC TTC AGA CTT CTG AAC CCA             850
      Ile Lys Arg Thr Arg Lys Gly Phe Arg Leu Leu Asn Pro
                          240

CTCAAGAAATATTTGCAACATTAGTTTTTTCCAGCATCAGCAATTGCTACT              940

AGGATTTATAGAAATGCTTCATTAAACTGAGTGAAACTGGTTAAGTGGCATG             1039

ATAGATTCATTTATTAGCATTTGTAAAGAGATGTTCAATTTCAATAAAATA              1138

AAAAAAAAAAAAA                                                    1198
```

POLYPEPTIDE AND DNA SEQUENCE CORRESPONDING TO THE HUMAN RECEPTOR WITH HIGH AFFINITY FOR IGE

BACKGROUND OF THE INVENTION

The receptor with high affinity for IgE (FcERI) is found exclusively on mast cells, basophils and related cells. Aggregation of IgE occupied FcERI by antigen triggers both the release of preformed mediators such as histamine and serotonin, as well as stimulating the synthesis of leukotrienes. It is the release of these mediators which result in the allergic condition, The most thoroughly characterized FcERI is that of the rat basophilic leukemia (RBL) cell line. It consists of three different subunits: (1) A 40–50 Kilodalton (Kd) glycoprotein alpha chain which contains the binding site for IgE, (2) A single 33 Kd beta chain and (3) Two 7–9 Kd disulfide linked Gamma chains. The gene for human FcERI has never been completely cloned and isolated. Only the gene coding for the alpha subunit of rat FcERI has been cloned and sequenced [see Kinet, et al., *Biochemistry,* 26:4605 (1987)]. The instant invention encompasses the cloning, sequencing and expression of the alpha subunit of the human FcERI.

SUMMARY OF THE INVENTION

The instant invention comprises a DNA sequence coding for the polypeptide corresponding to the alpha subunit of the human high affinity receptor for IgE (human FcERI).

The instant invention also comprises a polypeptide corresponding to the alpha subunit of human FcERI.

The instant invention also includes replicable prokaryotic or eukaryotic microbial expression vehicles capable of expressing the alpha subunit of the human FcERI polypeptide, transformed prokaryotic and eukaryotic microorganisms and cultures of these microorganisms which produce the alpha subunit of human FcERI polypeptide, as well as processes for producing the alpha subunit of the human FcERI polypeptide either through solid phase synthesis methods, or through the use of recombinant DNA technology in which the requisite gene sequences are inserted by means of a suitable DNA vector into a compatible prokaryotic or eukaryotic organism.

DETAILED DESCRIPTION

Figure 1A:
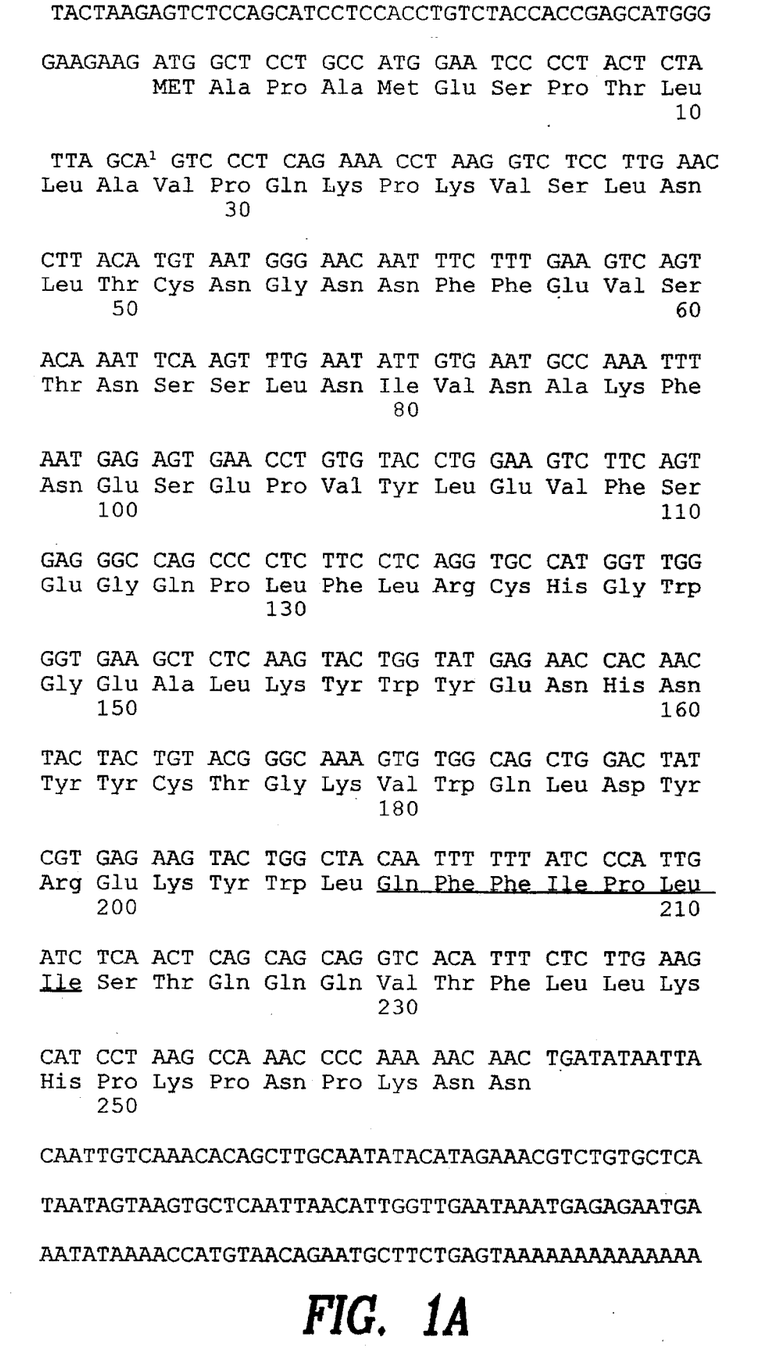
FIGS. 1A and 1B: show the nucleotide sequence and predicted amino acid sequence of human FcERI alpha cDNA.
Figure 1B:
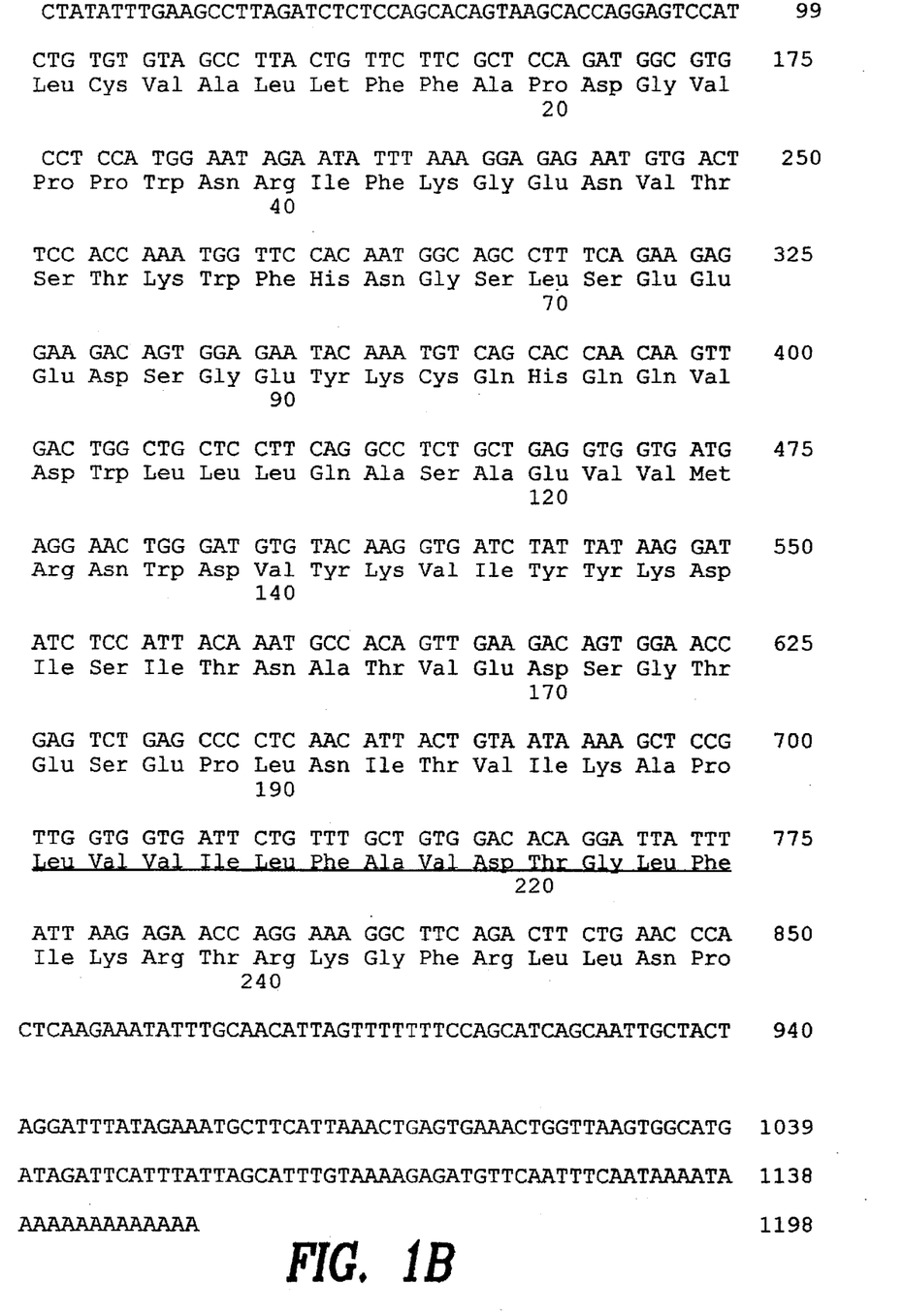

The DNA sequence which codes for the polypeptide corresponding to the alpha subunit of human FcERI is set forth in FIGS. 1A and 1B. This DNA is elucidated by probing a human peripheral blood leukocyte cDNA library with the corresponding rat FcERI DNA according to methods well known to those skilled in the art. The cDNA obtained by hybridization was then subcloned using standard techniques. These cDNA inserts were mapped by restriction enzyme analysis and further subcloned and sequenced. The result was a DNA sequence of approximately 1,200 bases which coded for the human FcERI alpha subunit.

In the application of current recombinant DNA procedures, specific DNA sequences are inserted into an appropriate DNA vehicle, or vector, to form recombinant DNA molecules that can replicate in host cells. Circular double-stranded DNA molecules called plasmids are frequently used as vectors, and the preparation of such recombinant DNA forms entails the use of restriction endonuclease enzymes that can cleave DNA at specific base sequence sites. Once cuts have been made by a restriction enzyme in a plasmid and in the segment of foreign DNA that is to be inserted, the two DNA molecules may be covalently linked by an enzyme known as a ligase. General methods for the preparation of such recombinant DNA molecules have been described by Cohen et al. [U.S. Pat. No. 4,237,224], Collins et al. [U.S. Pat. No. 4,304,863] and Maniatis et al. [Molecular Cloning: A Laboratory Manual, 1982, Cold Spring Harbor Laboratory]. Because they illustrate much of the state of the art, these references are hereby incorporated by reference.

Once prepared, recombinant DNA molecules can be used to produce the product specified by the inserted gene sequence only if a number of conditions are met. Foremost is the requirement that the recombinant molecule be compatible with, and thus capable of autonomous replication in, the host cell. Much recent work has utilized *Escherichia coli* (*E. coli*) as a host organism because it is compatible with a wide range of recombinant plasmids. Depending upon the vector/host cell system used, the recombinant DNA molecule is introduced into the host by transformation, transduction or transfection.

Detection of the presence of recombinant plasmids in host cells may be conveniently achieved through the use of plasmid marker activities, such as antibiotic resistance. Thus, a host bearing a plasmid coding for the production of an ampicillin-degrading enzyme could be selected from unaltered cells by growing the host in a medium containing ampicillin. Further advantage may be taken of antibiotic resistance markers where a plasmid codes for a second antibiotic-degrading activity at a site where the selected restriction endonuclease makes its cut and the foreign gene sequence is inserted. Host cells containing properly recombinant plasmids will then be characterized by resistance to the first antibiotic but sensitivity to the second.

The mere insertion of a recombinant plasmid into a host cell and the isolation of the modified host will not in itself assure that significant amounts of the desired gene product will be produced. For this to occur, the foreign gene sequence must be fused in proper relationship to a signal region in the plasmid for DNA transcription called a promoter. Alternatively, the foreign DNA may carry with it its own promoter, as long as it is recognized by the host. Whatever its origin, the promoter is a DNA sequence that directs the binding of RNA polymerase and therefore "promotes" the transcription of DNA to messenger RNA (mRNA).

Given strong promotion that can provide large quantities of mRNA, the ultimate production of the desired gene product will be dependent upon the effectiveness of translation from mRNA to protein. This, in turn, is dependent upon the efficiency of ribosomal binding to the mRNA. In *E. coli*, the ribosome-binding site on mRNA includes an initiation codon (AUG) and an upstream Shine-Dalgarno (SD) sequence, containing 3–9 nucleotides and located 3–11 nucleotides from the AUG codon, is complementary to the 3' end of *E. coli* 16S ribosomal RNA (rRNA) [Shine and Dalgarno, Nature 254:34 (1975)]. Apparently, ribosomal binding to mRNA is facilitated by base pairing between the SD sequence in the mRNA and the sequence at the 16S rRNA 3' end. For a review on maximizing gene expression, see Roberts and Lauer, Methods in Enzymology 68:473 (1979).

Most of the work in the recombinant DNA field to the present has focused on the use of bacterial expression systems such as *E. coli*. Yet, the use of bacterial cells has a number of undesirable aspects. For example, most proteins and polypeptides produced in *E. coli* accumulate in the periplasmic space. Recovery of these gene products thus requires disruption of the cells, a process which is inefficient and leads to a serious purification problem, as the desired product must be purified from the numerous other *E. coli* cellular constituents. Also, bacteria cannot carry out glycosylation which is needed to complete the synthesis of many interesting gene products or form the specific disulfide bonds which are essential for the proper conformation and biological activity of many eukaryotic proteins.

To overcome these deficiencies in bacterial expression systems, the attention of genetic engineers is increasingly turning to the use of eukaryotic host cells for recombinant DNA, not only to make desirable polypeptides and proteins but to study the control of gene expression as well. Cells such as yeast and mammalian cells can secrete desired gene products into the culture medium and can also carry out essential glycosylation processes. Yet, the use of mammalian cells for recombinant DNA cloning and expression also poses a host of technical obstacles that must be overcome. For example, the endogeneous plasmids that have proven to be so useful in bacteria are not replicated by higher eukaryotic cells. As a result, other approaches must be taken.

One approach has been to use the lower eukaryotic yeast, *Saccharomyces cerevisiae*, which can be grown and manipulated with the same ease as *E. coli*. Yeast cloning systems are available, and through the use of such systems the efficient expression in yeast of a human interferon gene has been achieved [Hitzeman et al., Nature (London) 293:717 (1981)]. Interferon genes do not contain introns, however, and it has been found that yeast cells do not correctly transcribe at least one heterologous mammalian gene that does contain introns, the rabbit β-globin gene (Beggs et al., Nature (London) 283:835 (1980)].

In another approach, foreign genes have been inserted into mammalian cells by means of direct uptake. This has been accomplished by calcium phosphate co-precipitation of cloned genes, by which procedure about 1–2% of the cells can generally be induced to take up the DNA. Such a low level of uptake, however, produces only a very low level of expression of the desired gene product. Where mammalian cells can be found which lack the thymidine kinase gene (tk⁻ cells), better results can be obtained by co-transformation. Tk⁻ cells, which cannot grow in selective HAT (hypoxanthine-aminopterin-thymidine) medium, can regain this lost enzymatic activity by taking up exogenous DNA (such as herpes simplex vital DNA) containing the tk gene through calcium phosphate co-precipitation. Other DNA covalently ligated to the tk DNA or merely mixed with it will also be taken up by the cells and will often be co-expressed [see Scangos et al., Gene 14:1 (1981)].

In a third approach, vital genomes have been used as vectors for the introduction of other genes into mammalian cells, and systems based upon Simian virus 40, papillomavirus and adenovirus genomes have been described [see P. W. J. Rigby, Expression of Cloned Genes in Eukaryotic Cells Using Vector Systems Derived from Vital Replicants, in Genetic Engineering, Vol. 3, R. Williamson, ed., Academic Press, New York, pp. 83–141 (1982) for a review]. These systems, however, suffer from the drawback of limited host cell range. Moreover, vital replication in these systems leads to host cell death. The use of retrovital DNA control elements avoids many of the disadvantages of these viral vector systems.

Gorman et al. [Proc. Natl. Acad. Sci. U.S.A. 79:6777 (1982)] have shown, for example, that the Rous sarcoma virus long terminal repeat (LTR) is a strong promoter that can be introduced into a variety of cells, including CV-1 monkey kidney cells, chicken embryo fibroblasts, Chinese hamster ovary cells, HeLa cells and mouse NIH/3T3 cells by DNA-mediated transfection.

The instant invention also comprises a polypeptide of the amino acid sequence corresponding to the alpha subunit of human FcERI.

The recombinant cDNA clone for human FcERI alpha chain was used to introduce these coding sequences into the appropriate eukaryotic expression vector in order to direct the synthesis of large amounts of the alpha chain polypeptide. In order for the alpha subunit to be expressed on eukaryotic cells it maybe necessary that the gene be complexed with that of the beta or gamma or other subunit. For expression of the secreted form this may not be necessary. Any of the appropriate eukaryotic expression vectors for example those set forth above, may be used. The expression of human FcERI alpha protein in eukaryotic cells will result in their synthesizing a mature IgE binding protein corresponding to human FcERI. The expression vectors may then be introduced into suitable eukaryotic cells by standard techniques. The synthesis of protein is monitored by demonstrating the ability of human IgE or rat IgE to bind to these cells.

The human FcERI alpha polypeptide may also be expressed in prokaryotic cells according to known methods. A recombinant cDNA clone for the human FcERI alpha chain is introduced into the appropriate prokaryotic expression vector to direct the synthesis of large amounts of IgE binding polypeptide derived from the alpha chain. This expression vector may then be transformed into suitable hosts and expression of a protein capable of binding to human IgE is then monitored.

Peptides corresponding to the complete or partial amino acid sequence of human FcERI alpha chain may also be synthesized by solid phase synthesis procedures for example, that generally described by Merrifield, *Journal of the American Chemical Society* 85, 2149 (1963). The peptide synthesized according to this method may be the entire alpha subunit or can be fragments which correspond to smaller, active portions of the alpha subunit.

The DNA sequences and polypeptides according to this invention exhibit a number of utilities including but not limited to:

1. Utilizing the polypeptide or a fragment thereof as an antagonist to prevent allergic response, or as a reagent in a drug screening assay.
2. Utilizing the polypeptide as a therapeutic.

3. Utilizing the polypeptide for monitoring IgE levels in patients.

4. Utilizing the DNA sequence to synthesize polypeptides which will be used for the above purposes.

5. Utilizing the DNA sequences to synthesize cDNA sequences to construct DNA probes useful in diagnostic assays.

The instant invention will be further described in connection with the following Examples which are set forth for the purposes of illustration only.

EXAMPLE I

Isolation of Human FcERI Alpha cDNA clones:

RNA was extracted from KU812 cells as described by Kishi, *Leukemia Research,* 9,381 (1985) by the guanidium isothiocyanate procedure of Chirgwin, et al., *Biochemistry,* 18,5294 (1979) and poly A+ RNA was isolated by oligo-dT chromatography according to the methods of Aviv, et al., *P.N.A.S. U.S.A.,* 69,1408 (1972). cDNA synthesis was performed as previously described Kinet, et al., *Biochemistry,* 26,2569 (1987). The resulting cDNA molecules were ligated to EcoRI linkers, digested with the restriction enzyme EcoRI, size fractionated and ligated to λgtll EcoRI arms as set forth in Young et al., *Science,* 222,778 (1983). The cDNA insert containing λgtll DNA was packaged into bacteriophage lambda particles and amplified on Y1090. A total of $1.2 \times 10^6$ independent cDNA clones were obtained. The cDNA library was plated onto Y1090 on 150 mm$^2$ plates ($10^5$ per plate) and transferred to nitrocellular filters. The cDNA library filters were screened by in situ hybridization using a nick translated cDNA fragment as in Kochan, et al., *Cell,* 44,689 (1986). The cDNA fragment was obtained from the rat FcERI alpha cDNA corresponding to nucleotides 119–781. Positive plaques were identified, purified and the cDNA inserts were subcloned, using standard techniques, into the pGEM vectors (Promega Biotech, Madison, Wis.). The cDNA insert was mapped by restriction enzyme analysis, subcloned into derivatives of pGEM and sequenced using the dideoxynucleotide method of Sanger et al., *P.N.A.S.,* 74,5463 (1977) following the GemSeq double strand DNA sequencing system protocol from Promega Biotech (Madison, Wis.). The DNA sequence was determined for both strands of the cDNA clone pLJ663 (nucleotides 1–1151) and for 300 bp of each end of clone pLJ 587 (nucleotides 658–1198). No discrepancy in DNA sequence between the two cDNA clones was observed.

Figure 2A:
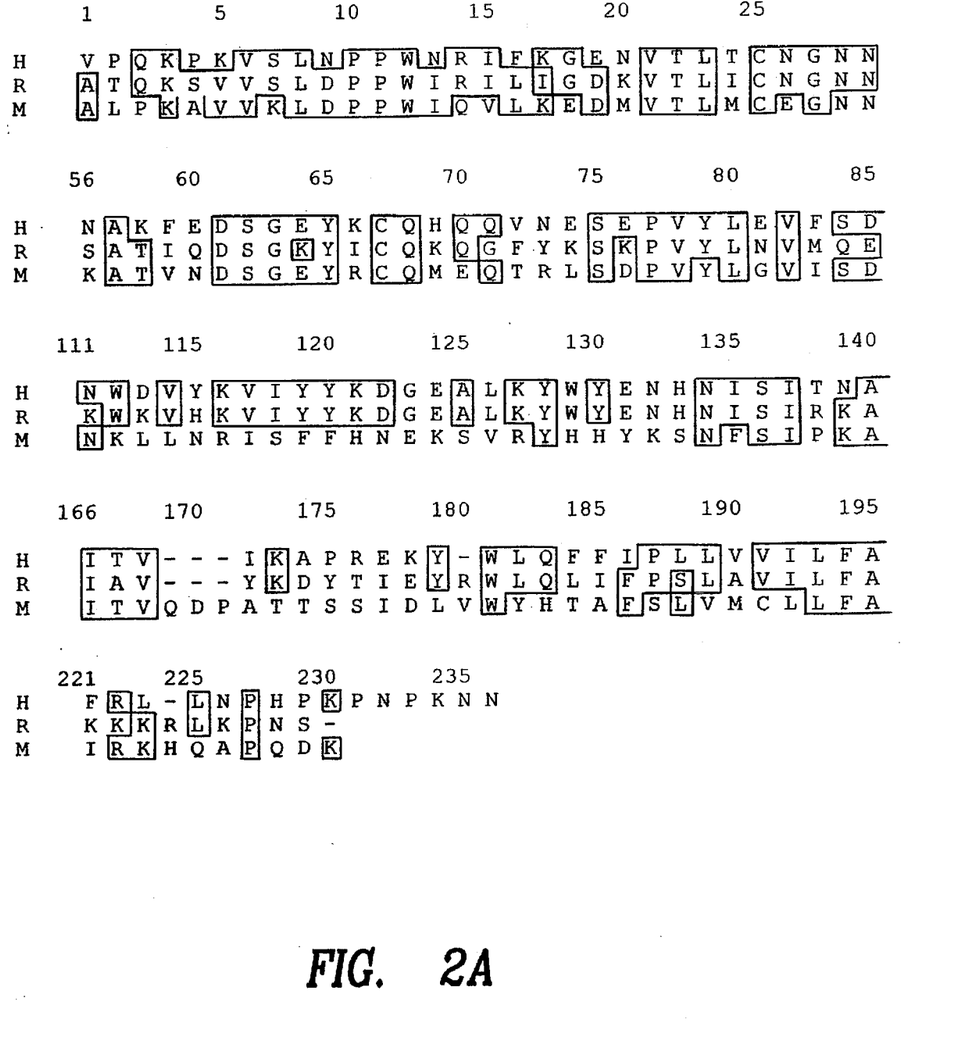
FIGS 2A and 2B: show the amino acid sequence homology of rat FcERI alpha subunit (R), human FcERI alpha subunit (A), and mouse FcERI alpha subunit (M). The regions of identity between the three are boxed. The number one position corresponds to the site of the predicted mature N-terminus of each protein.
Figure 2B:
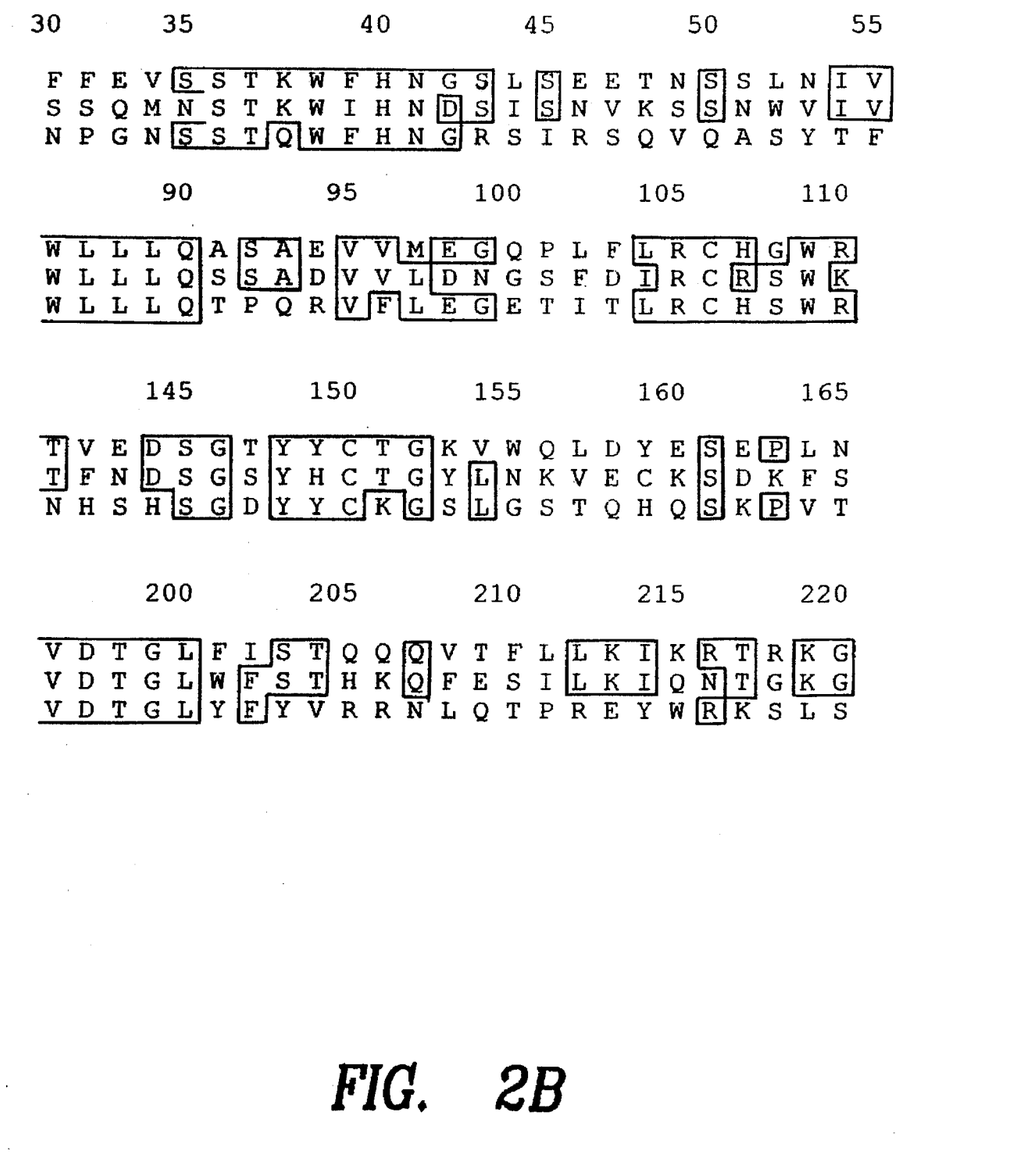

The sequence for the human FcERI alpha cDNA is presented in FIGS. 1A and 1B. The predicted amino acid sequence for the human FcERI alpha polypeptide is shown below the nucleotide sequence, beginning with methionine at nucleotide 107–109 and ending with asparagine at nucleotide 875–877. The site of the predicted mature N-terminus was determined to be valine at nucleotide 182–184 according to the rules set forth by von Heijne, *Eur. Journal of Biochem:* 133,17: and *Nucleic Acid Research,* 14,4683 (1986). This predicts a 25 amino acid signal peptide. The rest of the cDNA sequence suggests that the human FcERI alpha chain contains a 179-residue extracellular portion (amino acid residues 26–204) with 2 homologous domains (14 out of 25 residues are identical residues 80–104 and 163–190), a 20-residue transmembrane segment (residues 205–224) and a 33 residue cytoplasmic domain containing 8 basic amino acids. Overall, there is 49% identity between the human and rat FcERI alpha sequences, and 37% identity between the human FcERI alpha and mouse FcGR alpha (FIGS. 2A and 2B). The greatest level of homology is within the transmembrane region where 9 amino acids surrounding the common aspartic acid residue are identical.

EXAMPLE II

Figure 3:
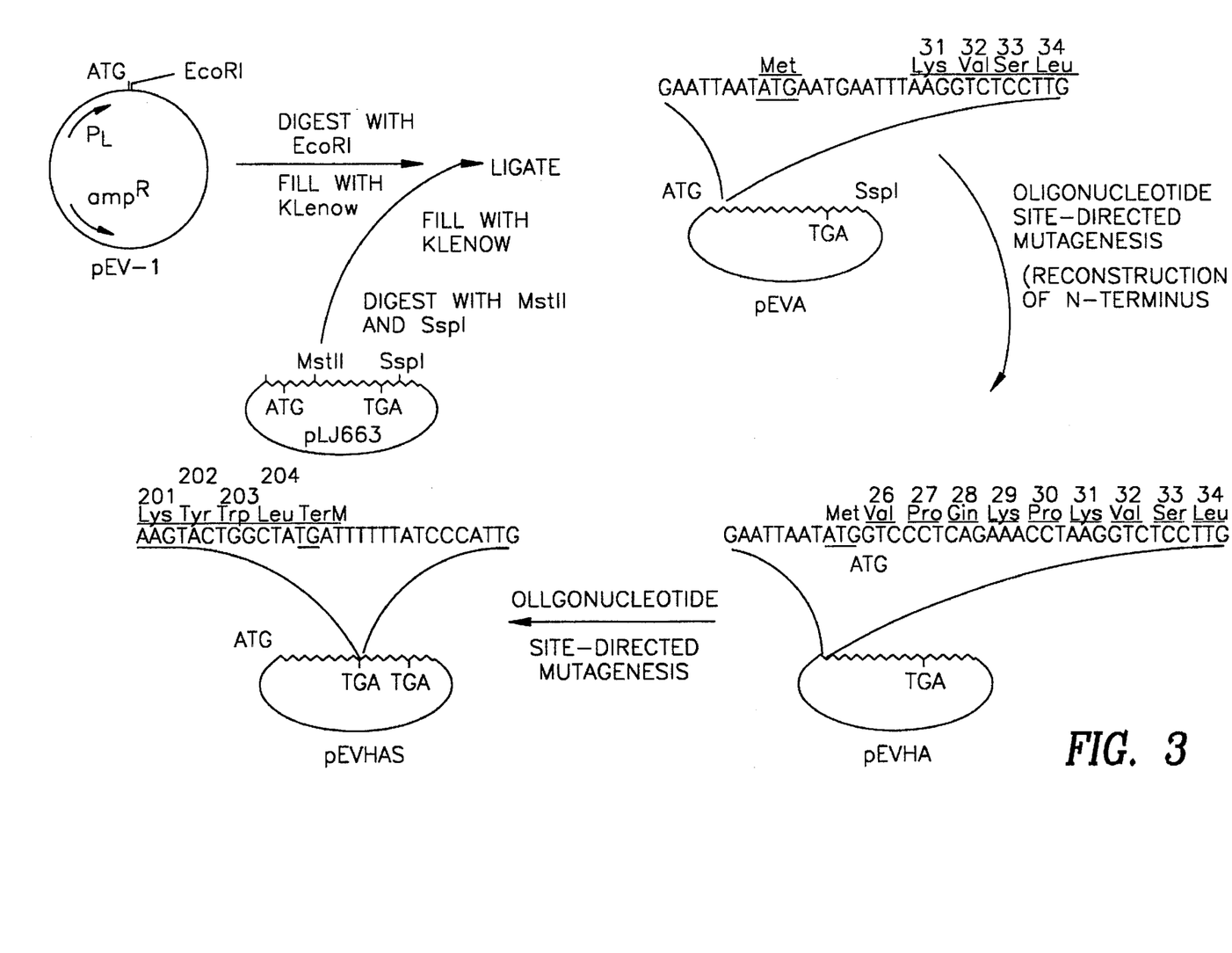
FIG. 3: is a flow chart showing the construction of eukaryotic expression vectors which direct the synthesis of a complete biologically active FcERI alpha chain (pHAI, pHAII) or a soluble, secreted, biologically active FcERI alpha chain (pHASI, pHASII).
Figure 4:
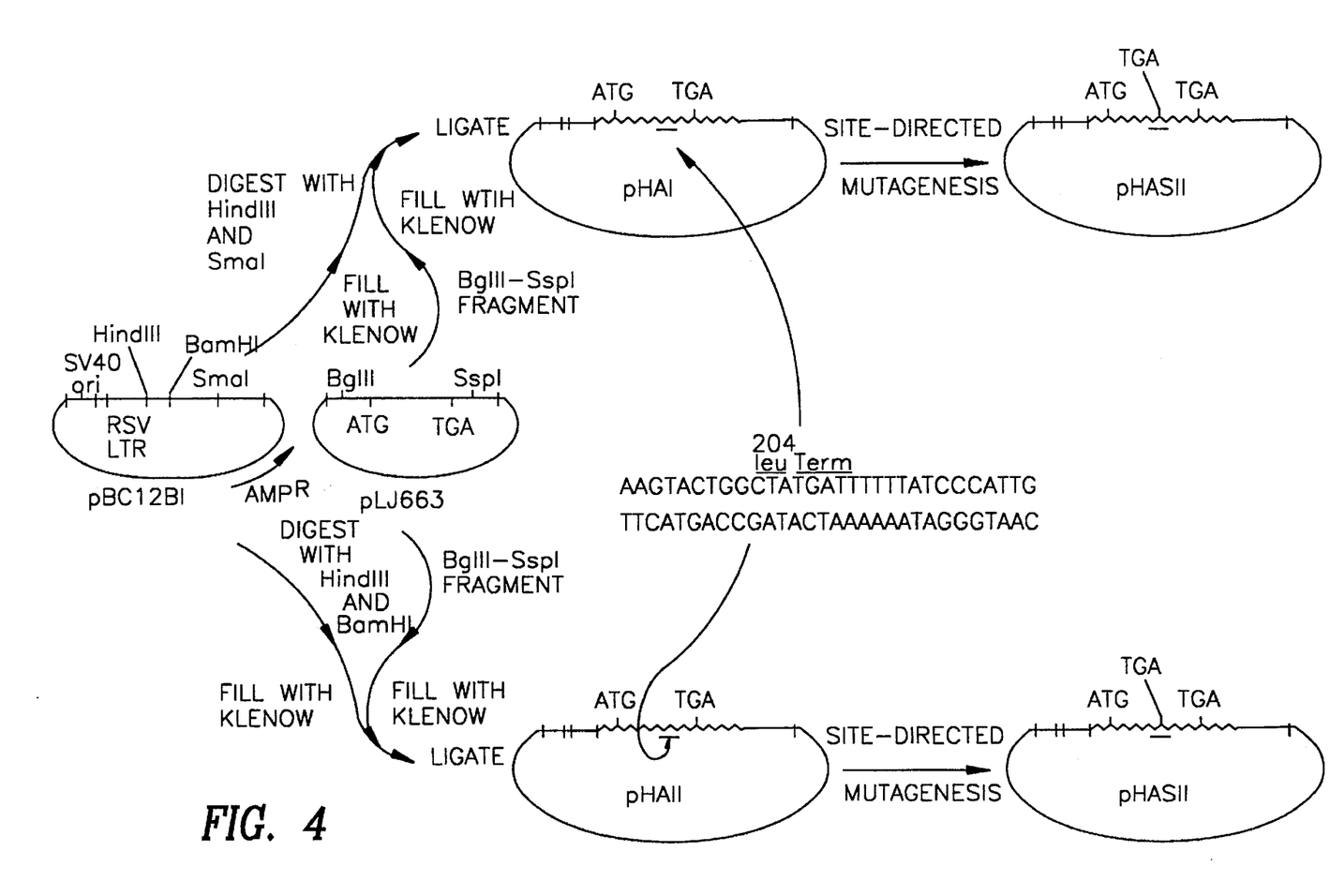
FIG. 4: is a flow chart showing the construction of a prokaryotic expression vector which directs the synthesis of a soluble, biologically active FcERI alpha chain (which consists of amino acid residues 26–204).

Expression of the Human FcERI Alpha Complete and Soluble Forms in Eukaryotic Cells Using the recombinant cDNA clone for the human FcERI alpha chain, it is possible to introduce these coding sequences into an appropriate eukaryotic expression vector to direct the synthesis of large amounts of both a complete and soluble form of the alpha chain. For surface expression it may be necessary that the alpha subunit be complexed with the beta or gamma subunit whereas for the eukaryotic expression of the secreted form of the alpha subunit this may not be necessary. An appropriate vector for the purpose is pBC12BI which has previously been described in Cullen, (1987) *Methods in Enzymology* 152, Academic Press, 684. Construction of expression vectors coding for the complete alpha chain can be isolated as follows (FIG. 3): A unique BglII–SspI fragment (nucleotides 65–898) is isolated from pLJ663, the BglII end is filled in with DNA polymerase I Klenow fragment and ligated into pBC12BI which has been restricted with either HindIII-BamHI or HindIII-SmaI (the ends are made blunt by filling in with DNA polymerase I Klenow fragment). The reason for attempting two different constructions is that the former contains a 3' intron while the latter does not. The presence or absence of introns may affect the levels of alpha protein which are synthesized in cells transfected by these vectors. Construction of expression vectors coding for the soluble form of the alpha chain would be accomplished by introducing a termination codon at nucleotides 719–721 of the coding region in the alpha chain of the expression vectors noted above (pHAI, pHAII, FIG. 3). This would remove the putative transmembrane and cytoplasmic regions resulting in the synthesis of a secreted soluble form of the human alpha chain. Introduction of a termination codon is accomplished by oligonucleotide-directed site specific mutagenesis as outlined by Morinaga et al., *Bio. Tech.,* 2,636 (1984). The sequence of the oligonucleotide will be 5' AAGTACTGGCTATGATTTTTTATC-CCATTG 3'. The resulting expression vectors are pHASI and pHASII (FIG. 3) and these will direct the synthesis of a truncated alpha protein corresponding to amino acids 1–204. Expression of this protein in eukaryotic cells will result in synthesis of a mature, IgE binding protein encompassing amino acid residues 26–204.

The expression vectors are then introduced into suitable eukaryotic cells such as CHO or COS by standard techniques such as those set forth in Cullen, (1987), *Methods in Enzymology,* 152, Academic Press, New York p. 684, in the presence of a selectable marker such as G418 or Methotrexate resistance. The selectable marker for Methotrexate resistance has an added advantage, since the levels of expression can be amplified by introducing the cells to higher levels of drugs. The synthesis of protein is monitored by demonstrating the ability of human IgE (or rat IgE) to bind to these cells (in the case of the complete alpha chain), or in the case of the soluble form of the alpha chain, to demonstrate that the protein secreted from these cells has the ability to bind IgE in the presence or absence of the beta.

EXAMPLE III

Expression of the Human FcERI Alpha Soluble in Prokaryotic Cells

Using the recombinant cDNA clone for the human FcERI alpha chain, it is possible to introduce these coding 
sequences into an appropriate prokaryotic expression vector to direct the synthesis of large amounts of a soluble (non-membrane bound) IgE binding polypeptide derived from the alpha chain. An appropriate vector for this purpose is pEV-1 which has been described by Crowl, et al., *Gene,* 38.31 (1985). Construction of an expression vector coding for a soluble alpha chain can be isolated as set forth in FIG. 4: a unique MstII-sSpI fragment (nucleotides 195–898) is isolated from pLJ663, the MstII end is filled in with DNA polymerase I Klenow fragment and ligated into pEV-1 which has been restricted with EcoRI, and the ends filled in with Klenow (FIG. 4, pEVA). The N-terminus of the mature alpha chain is reconstructed by oligonucleotide directed-site specific mutagenesis. The sequence of the oligonucleotide will be 5' GAATTAATATGGTCCCTCAGAAAC-CTAAGGTCTCCTTG 3'. Introduction of this sequence into the expression vector pEVA aligns the Methionine residue of the EV-1 vector next to Valine-26 (the predicted mature N-terminus of the alpha chain) followed by amino acid residues 27–204 (pEVHA, FIG. 4). Reconstruction of the soluble form FcERI alpha is accomplished by oligonucleotide site-directed mutagenesis. The sequence of the oligonucleotide will be 5'-AAGTACTGGCTATGATTTTTTATCCCATTG -3'. Introduction of this sequence into the expression vector, terminates polypeptide synthesis just prior to the start of the transmembrane region. The protein thus encoded by the expression vector pEVHAS, should faithfully direct the synthesis of a soluble form of the alpha chain, corresponding to amino acid residues 26–204.

This expression vector is then transformed into suitable hosts.

While the invention has been described in connection with the preferred embodiment, it is not intended to limit the scope of the invention to the particular forms set forth, but, on the contrary, it is intended to cover such alternatives, modifications, and equivalents as may be included within the spirit and scope of the invention as defined by the appended claims.

We claim:

1. A cDNA molecule coding for a polypeptide comprising the alpha subunit of the human high affinity receptor for IgE (FcERI).

2. The cDNA molecule of claim 1 operably linked with a DNA sequence capable of effecting microbial expression of a polypeptide comprising the alpha subunit of the human FcERI.

3. A replicable microbial expression vector containing the cDNA molecule of claim 1.

4. A microorganism transformed with a microbial expression vector which vector contains the cDNA molecule of claim 1.

5. The microorganism of claim 4 which is eukaryotic.

6. The microorganism of claim 4 which is prokaryotic.

7. A cDNA molecule coding for a polypeptide consisting of amino acids 26–204 of FIG. I.

* * * * *